(12) United States Patent  
Aizenfeld et al.

(10) Patent No.: US 8,449,457 B2  
(45) Date of Patent: May 28, 2013

(54) OPTICAL HEAD FOR ENDOSCOPE

(75) Inventors: Amram Aizenfeld, Kibbutz Ramot Menashe (IL); Victor Levin, Haifa (IL); Omer Shezifi, Haifa (IL); Dan Oz, Even Yehuda (IL); Yuri Gershov, Haifa (IL); Leonid Krivopisk, Nesher (IL); Yakov Bar-Or, Haifa (IL)

(73) Assignee: Stryker GI Services C.V., Waardenburg (NL)

( * ) Notice: Subject to any disclaimer, the term of this patent is extended or adjusted under 35 U.S.C. 154(b) by 1925 days.

(21) Appl. No.: 11/218,289

(22) Filed: Sep. 1, 2005

(65) Prior Publication Data

US 2006/0063976 A1   Mar. 23, 2006

Related U.S. Application Data

(60) Provisional application No. 60/606,976, filed on Sep. 3, 2004, provisional application No. 60/626,382, filed on Nov. 9, 2004.

(51) Int. Cl.  
*A61B 1/06* (2006.01)

(52) U.S. Cl.  
USPC .......................................... 600/160; 600/180

(58) Field of Classification Search  
USPC ................................. 600/175–182  
See application file for complete search history.

(56) References Cited

U.S. PATENT DOCUMENTS

| | | | |
|---|---|---|---|
| 5,419,310 A | 5/1995 | Frassica | |
| 5,518,501 A * | 5/1996 | Oneda et al. | 600/127 |
| 5,746,694 A | 5/1998 | Wilk et al. | |
| 5,916,145 A | 6/1999 | Chu | |
| 6,239,909 B1 | 5/2001 | Hayashi et al. | |
| 6,449,006 B1 * | 9/2002 | Shipp | 348/70 |
| 6,533,722 B2 * | 3/2003 | Nakashima | 600/179 |
| 6,551,240 B2 | 4/2003 | Henzler | |
| 6,569,088 B2 | 5/2003 | Koshikawa | |
| 6,655,377 B2 | 12/2003 | Pacey | |
| 6,730,019 B2 | 5/2004 | Irion | |
| 7,229,407 B2 * | 6/2007 | Suzushima | 600/179 |
| 7,316,647 B2 * | 1/2008 | Kimoto et al. | 600/179 |
| 7,452,328 B2 * | 11/2008 | Homan et al. | 600/180 |
| 2001/0023312 A1 | 9/2001 | Pacey | |
| 2002/0143239 A1 | 10/2002 | Henzler | |
| 2003/0028078 A1 * | 2/2003 | Glukhovsky | 600/109 |
| 2003/0032860 A1 | 2/2003 | Avni | |
| 2003/0117491 A1 * | 6/2003 | Avni et al. | 348/77 |
| 2003/0130562 A1 * | 7/2003 | Barbato et al. | 600/109 |
| 2004/0064018 A1 | 4/2004 | Dunki-Jacobs | |
| 2004/0102680 A1 | 5/2004 | Sasaki | |
| 2005/0003323 A1 | 1/2005 | Katsuda et al. | |
| 2005/0124858 A1 * | 6/2005 | Matsuzawa et al. | 600/176 |
| 2006/0047184 A1 * | 3/2006 | Banik et al. | 600/156 |

FOREIGN PATENT DOCUMENTS

WO   WO 03/098913   11/2003

* cited by examiner

*Primary Examiner* — Philip R Smith  
(74) *Attorney, Agent, or Firm* — Nath, Goldberg & Meyer; Jerald L. Meyer; Scott Langford

(57) ABSTRACT

An optical head for an endoscope is fitted with an imaging system comprising a solid state imaging sensor and with an illuminating system comprising illuminating means, e.g. LED's. At least one illuminating means is defined by a parameter, which value is different from the value of the same parameter of the remaining illuminating means. Among the parameters are luminous intensity, luminous intensity distribution angle, and direction of the longitudinal axis of the illuminating means.

19 Claims, 8 Drawing Sheets

OPTICAL HEAD FOR ENDOSCOPE

FIELD OF THE INVENTION

The present invention relates generally to the field of endoscopy and specifically to an optical head for an endoscopic apparatus used in colonoscopic procedures during which a flexible tube is inserted into the rectum and colon for examination of the colon interior for abnormalities. It should be kept in mind, however, that the present invention is not limited strictly to the optical head used in the colonoscopic procedure. The present invention is intended for visualization of the interior of a body passage, lumen or cavity as might be required during any other endoscopic procedure associated with examination, operation, diagnostic, etc.

BACKGROUND OF THE INVENTION

There are known various endoscopic apparatuses employing optical heads for visualization of the interior of the body cavity or lumen. Essential parts of such optical head are imaging system and illumination system. The imaging system might comprise an objective lens at the distal end of the endoscope and an eyepiece at the proximal end of the endoscope to observe the interior of the lumen with the eye.

In the modern endoscopic devices the imaging system comprises an imaging optic and a solid state imaging sensor, e.g. in the form of a CCD-chip or CMOS, which transforms the light signals reflected from the object into electric signals, passing to proximal end via electric lines and visually presented, as a real image, on an image reproduction unit outside the endoscope.

The illumination system serves for transmitting light to distal end of the endoscope to illuminate the location to be observed. Such illumination system might comprise external light sources, e.g. xenon or halogen light sources with fiber optic bundle for submitting light energy from light source to endoscope distal tip or internal light sources, e.g. light emitting diodes (LED's) located within the endsocope.

The use of CCD sensors or CMOS and LED's in optical head of an endoscope is relatively new issue, nevertheless one can mention many patents describing endoscopes provided with such optical devices.

An example of an endoscope with LED illumination can be found in Nakashima (U.S. Pat. No. 6,533,722). In this endoscope the LED's are located within the endoscope shaft and at a distal end thereof. The LED's are arranged such that a part of them is seen so as to overlap with the CCD when viewed from the optical axis direction of the imaging system. By virtue of this provision it is possible to reduce the diameter of the distal end of the endoscope.

Another example of an endoscope provided with a CCD chip and LED's is disclosed in Irion (U.S. Pat. No. 6,730,019). In this endoscope the imaging system (fiber bundle or a CCD sensor) is also located within the shaft, while the LED's are arranged at the proximal end of the endoscope outside of the shaft. The LED's are selected in such a manner that they emit light in different spectral ranges to produce additive mixture of the light.

By virtue of this provision the image acquired by the endoscope is colored as faithfully as possible.

Still further examples of endoscopes employing CCD sensor and LED illumination are disclosed in Pacey (U.S. Patent Publication 2001/0023312), Shipp (U.S. Pat. No. 6,449,006), Henzler (U.S. Patent Publication 2002/0143239), Pacey (U.S. Pat. No. 6,655,377), Henzler (U.S. Pat. No. 6,551,240), Dunki-Jacobs (U.S. Patent Publication 2004/0064018), and Sasaki (U.S. Patent Publication 2004/0102680).

The present invention concerns an optical head, in which a CCD or camera or CMOS is employed in the imaging system and several LED's as part of the illuminating system.

Even though the use of a CCD chip or CMOS and LED's brings many advantages, nevertheless the quality of image acquired with such optical system might require improvement. The reason for this is the illumination nonuniformity due to the excessive or insufficient illumination of various locations in the body lumen. The illumination nonuniformity significantly limits the distance along which a good picture can be acquired. The other problem, which arises in the optical heads provided with the LED illumination, is associated with the situation when the longitudinal axis of the optical head is not parallel with the longitudinal axis of the body lumen or cavity. This problem often arises when the doctor displaces the endoscope within the body lumen. As a result of this displacement various locations of the observable area are illuminated with different intensity and it is difficult to acquire good pictures of the whole observed area.

In Avni (U.S. Patent Publication 2003/0032860) is described a video rectoscope equipped with a video camera head which has a color CCD array and several white LED's. The rectosope is manufactured commercially by SightLine Technologies Ltd. as a RectoSight® Disposable Video Rigid Rectoscope. In this optical head each LED is defined by a luminous intensity distribution angle of about 40 degrees. This value of the distribution angle is sufficient for acquiring a good picture along a maximal distance of 50-70 mm. Though such a distance is quite reasonable for a rectoscopic application it might be too short for the colonoscopic procedure.

In Koshikawa (U.S. Pat. No. 6,569,088) is described an endoscope apparatus, in which a problem of excessive halation due to illumination nonuniformity is solved by providing an optical head with two or more types of illumination optical systems having different light strength.

The difference in the light strength is achieved by virtue of several illumination lens systems with a positive or negative power and a diffusion element arranged at the object side. This solution is implemented in an optical head, which employs fiber bundles instead of LED's.

Thus, despite there are known many attempts to devise an endoscope optical head, which uses LED's for illumination, nevertheless there still exists a need for a new and improved optical head, which allows improving the illumination uniformity perceived by CCD or CMOS sensor and thus to increase the distance along which a good picture can be acquired irrespective whether the longitudinal axis of the optical head is parallel or not with the longitudinal axis of the body lumen.

For a better understanding of the present invention as well of its benefits and advantages, reference will now be made to the following description of its embodiments taken in combination with the accompanying drawings.

DETAILED DESCRIPTION OF THE INVENTION

Figure 1:
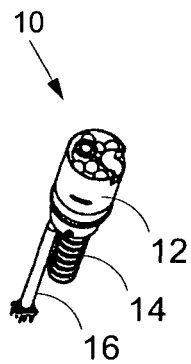
FIG. 1 is an isometric view of an embodiment of the optical head of the invention.

With reference to FIG. 1 a first embodiment of an optical head 10 for an endoscopic apparatus, preferably a colonoscopic apparatus, is shown. The other components of the colonoscopic apparatus, e.g. insertion tube with working channel and navigation mechanism, operating handle, control unit, video console with monitor etc. are not shown, but is should be appreciated that the optical head is deployed within an insertion tube and at a distal end thereof. The optical head comprises a main body portion 12 connected with a guide channel 14 of the endoscope. The main body portion is electrically connected to a screen by a cable 16, which, in its turn, communicates with a video console for energizing and controlling the head functions and for displaying an image of a body lumen captured thereby.

Figure 2:
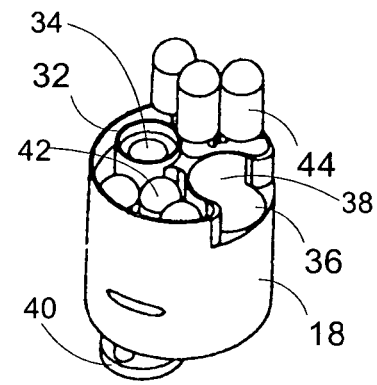
FIG. 2 is an exploded, enlarged isometric view of the optical head shown in FIG. 1.
Figure 2:
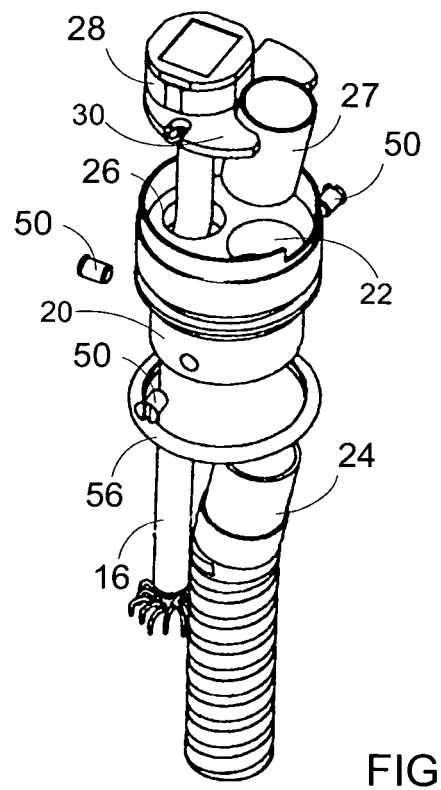

Referring now to FIG. 2, it is seen that the main body portion comprises a frontal portion 18, which is detachably connectable with a rear portion 20. Within the rear portion is provided a through going bore 22 for insertion thereinto of a frontal end 24 of the guide channel 14. In the rear body portion is made a through going bore 26 for the cable 16. Electrically connected to the cable is a CCD sensor 28 attached to a printed circuit board 30. Instead of the CCD sensor any other appropriate sensor, e.g. a CMOS sensor, can be used. The CCD sensor collects light energy, transfers it into analog signals which pass to the video processor of the video console unit, where those signals are converted into a video signal such as PAL/NTSC/RGB etc. and displayed. Securable on the frontal end 24 of the guide channel an extension insert 27 is provided. This insert serves for sealing the passage between the guide channel and the head, after the guide channel is inserted within the rear portion.

The frontal portion 18 is provided at its distal end with an aperture 32. The aperture accommodates therein an objective lens 34, which observes through the aperture those locations of the body lumen, which are in front of the aperture. Within the frontal portion a passage 36 is made, which terminates by a U-like depression 38 situated at the distal end of the frontal portion. Once the frontal and the rear portion are assembled the passage accommodates therein the extension insert 27 while the U-like depression serves as an exit for a working channel, or so called multilumen tubing, which extends along the guide channel.

Situated at the proximal end of the frontal portion and opposite to the lens an optical filter 40 is provided. It can be appreciated that due to the U-like depression 38 the distal end of the frontal portion has a configuration, which cross-section is defined by two symmetrically disposed arched regions. Deployed within the distal end of the frontal portion an illumination module with two groups of illumination means, preferably white LED's, is provided. It should be kept in mind that instead of or in addition to white LED's other LED's can be employed.

Construction of the module will be explained further with reference to FIG. 5, 8, 9. In practice each group of LED's consists of three LED's, which are designated by the corresponding common reference numerals 42, 44. The groups are arranged within the module in such a manner that each group resides within respective arched region provided at the left or the right side of the window. The LED's are arranged within the module in such a manner that the middle LED is closer to the window, while the remaining two LED's are situated closer to the circumferential wall of the head body portion. It is not shown in details but should be appreciated that the LED's reside on a mounting plate and are electrically connected to the printed circuit board 30 as it is known in the art.

Figure 3:
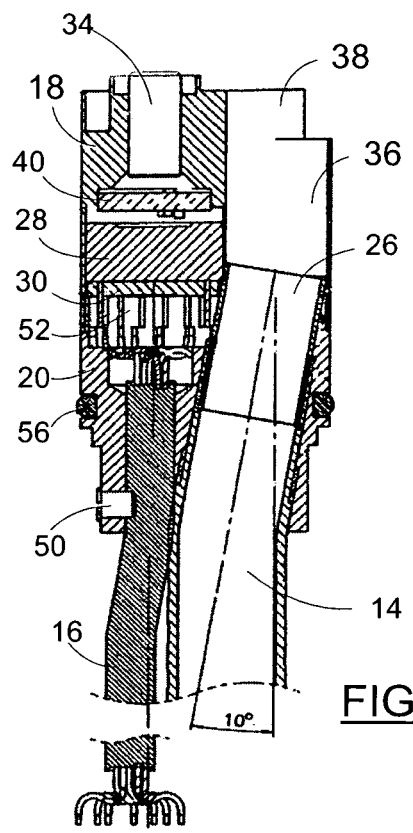
FIG. 3 is an enlarged, longitudinal cross-sectional view of the optical head shown in FIG. 1.
Figure 4:
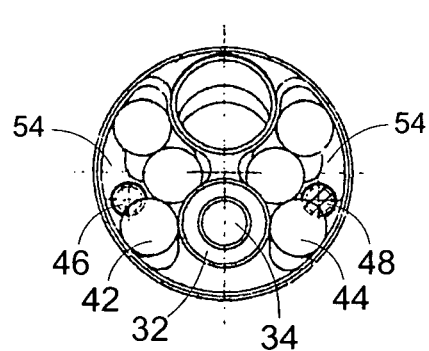
FIG. 4 is an enlarged, front view of the optical head shown in FIG. 1.

Referring now to FIG. 3 and FIG. 4 it is seen the optical head of the invention, after its frontal and rear portions are connected by longitudinally directed screws 46, 48. Besides there are provided also transversally directed screws 50, which connect the rear portion of the head with vertebrae of a navigation mechanism usually deployed in the bending section of the insertion tube. This mechanism is known per se and is not shown.

Furthermore seen in FIG. 3 is a plurality of contact legs 52 referring to various electronic components of the CCD sensor. The legs protrude from the circuit board and are electrically connected to the cable 16 for example by soldering. It is not shown, but should be appreciated that the LED's are also provided with legs, which are electrically connected to the cable through the printed circuit board.

As seen in FIG. 4 free space 54 is provided between the LED's and the circumferential wall of the main body portion. In practice this space is filled by appropriate filler, e.g. epoxy resin. By virtue of this provision, the position of each LED within the head remains fixed. The filler also fills free space between the printed circuit board and the cable.

An O-ring 56 is also seen in FIG. 3, which allows sealing engagement of the optical head with a disposable cap (not shown). This cap might be required for those endoscopes, which are provided with a disposable inflatable propelling sleeve as described in our previous patent applications, e.g. PCT/IL03/00661 or U.S. Ser. No. 60/570,607 herein incorporated by reference.

In accordance with the present invention the LED's employed in the optical head are deliberately selected such that they are defined by different luminous intensity and/or by different luminous intensity distribution angle. Here, by luminous intensity (also known as light strength) is meant the amount of light power emanating from a point source within a solid angle of one steradian. By luminous intensity distribution angle is meant a half-intensity beam angle, given in degrees, which characterizes how far in degrees from the on-axis perspective luminous intensity of a particular LED drops to 50 percent in both directions from the axis. This characteristic, which sometimes is called directivity, presents graphically in polar or Cartesian coordinates how relative luminous intensity depends on the viewing angle. This characteristic can vary depending on the axial orientation of the LED.

Figure 5:
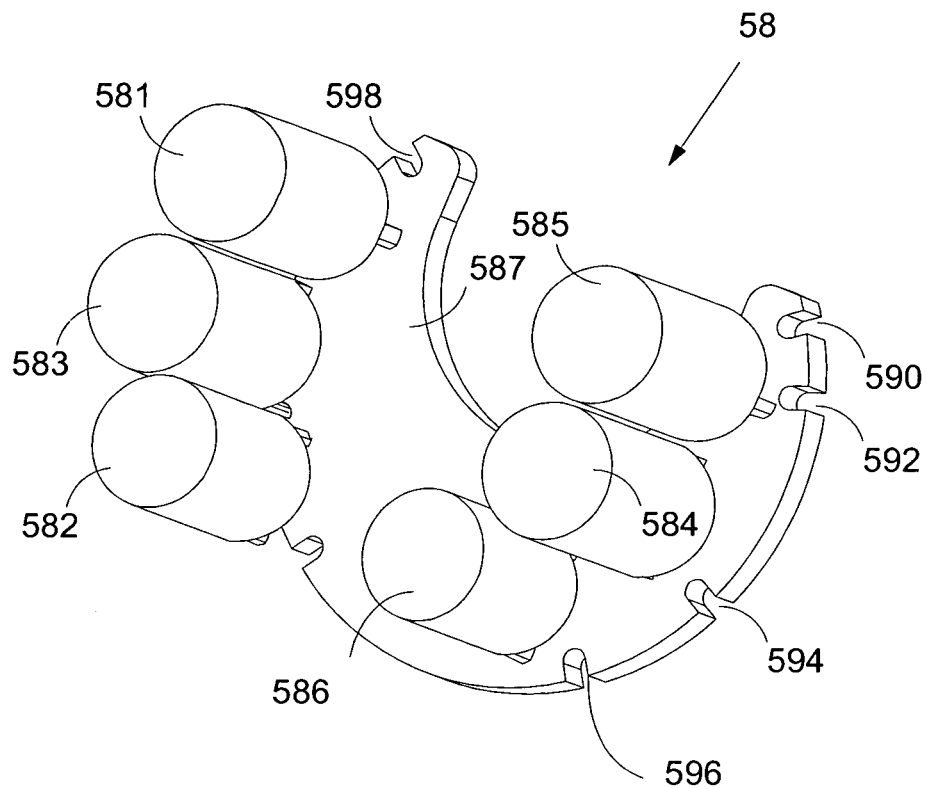
FIG. 5 shows an illuminating module of the invention.

In FIG. 5 is shown an example of an illumination module employed in the optical head of the invention. The module is designated by reference numeral 58 and it is seen that it comprises six white LED's 581, 582, 583, 584, 585, 586, soldered to a saddle-like mounting plate 587. Similarly to the module described in the embodiment shown in FIG. 2, the LED's are divided into two groups, which are disposed on the mounting plate. However in contrast to the previous arrangement it is seen that the middle LED's 583, 584 are located closer to the outside periphery of the module. This arrangement might have some advantage, since it provides more room for the LED's and accordingly LED's of larger diameter could be employed.

On the periphery of the mounting plate are made several cutouts to allow passing metallic contacts through the plate. The contacts lead to each LED and to the ground. The cut-outs designated by reference numerals 590 and 598 are reserved for grounding, while cutouts 592, 594, 596 are reserved for respective LED's 585, 584, 586. There are also cutouts referring to the opposite group of LED's, but they are not seen in this view. In practice the mounting plate can be manufactured from ceramics as a hybrid module comprising a CCD-chip having its bulk and the surface occupied by the necessary electronic components and by the contacts for LED's. One of the advantages of such a ceramic hybrid module would be its good thermal conductivity, thereby efficiently dissipating the heat accumulated during the LED's operation and thus prolonging the optical head's service life.

According to one aspect of the invention, the LED's which have similar luminous intensity distribution angle are secured on the mounting plate so as to be directed parallel to each other and to the longitudinal axis of the optical head. At the same time the LED's defined by dissimilar luminous intensity distribution angle are selected in such a manner that two middle LED's 583, 584 are defined by a luminous intensity distribution angle, which is wider than the luminous intensity distribution angle of the outside LED's 581, 582, 585, 586. In practice the middle LED's should have a luminous intensity distribution angle of about 60-100 degrees, while the outside LED's should have a luminuous intensity distribution angle of about 15-25 degrees. By virtue of this provision, it is possible to achieve very homogeneous illumination of a body lumen or other body cavity, which diameter is between 20-30 mm. This homogeneous illumination permits acquiring good quality pictures from those locations, which are remote from the optical head either by a long distance of 100-140 mm or by a middle distance of 20-30 mm or by a short distance of 5-10 mm. As suitable LED's, which can be advantageously used in this embodiment one can mention LED's manufactured by Nichia Corporation, Japan.

The above-described embodiments provide good solution for the situation, in which the longitudinal axis of the optical head is substantially co-axial with the axis of the body lumen.

Figure 6:
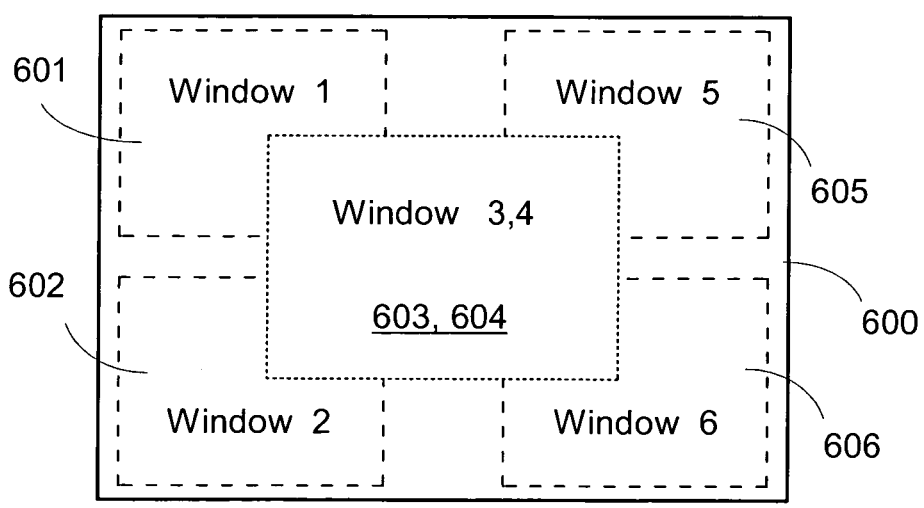
FIG. 6 schematically shows division of the field of view of the CCD camera into virtual regions.
Figure 7:
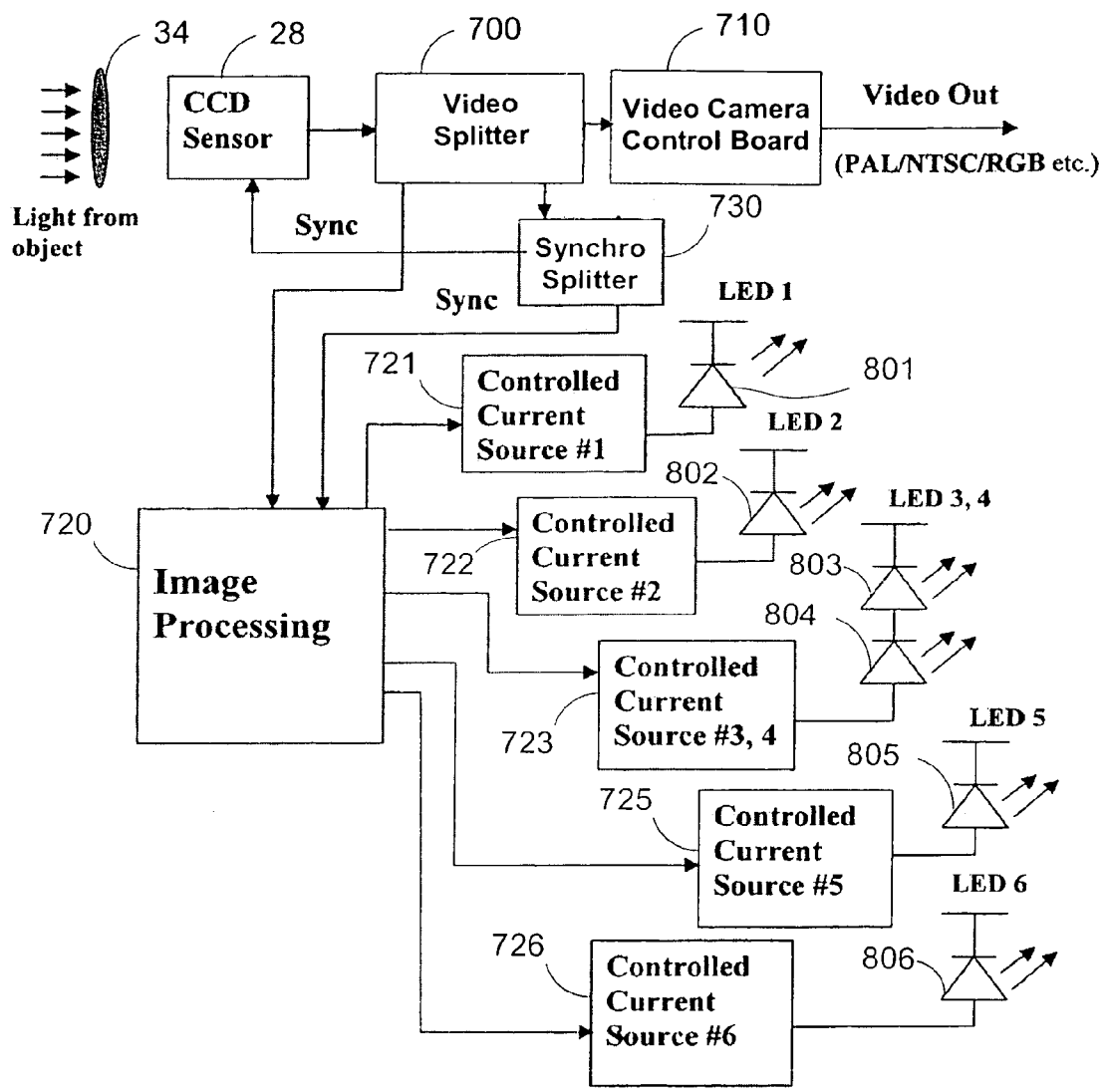
FIG. 7 is a block diagram of the control system of the illuminating module.
Figure 8:
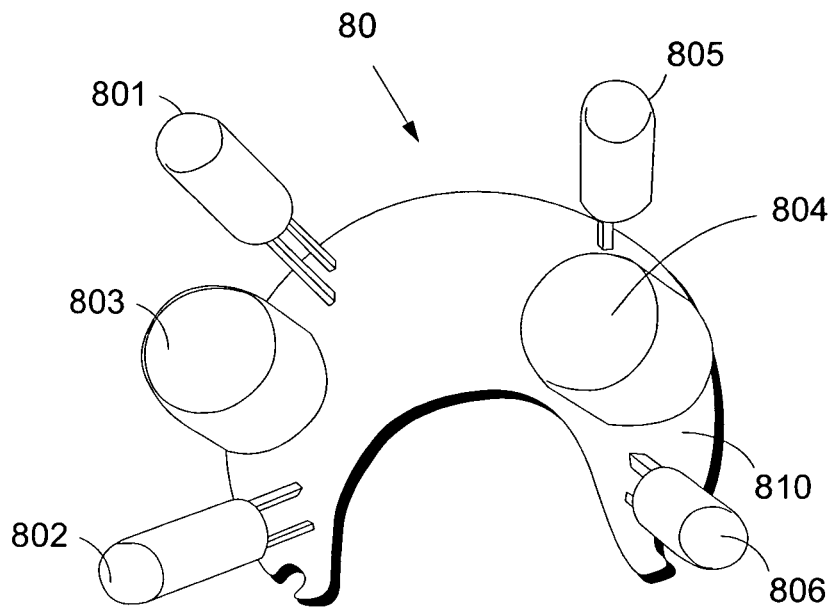
FIG. 8 shows an illuminating module in accordance with another embodiment of the invention.

However, in the situation when the longitudinal axis of the optical head is tilted with respect to the body lumen axis, another embodiment of the present invention might provide appropriate solution. According to this embodiment, which is shown in FIGS. 6, 7 and 8, the optical head is provided with an illumination module 80 (seen in FIG. 8), which employs six LED's arranged on a saddle-like mounting plate 810 in a pattern, which is similar to the embodiment shown in FIG. 5. Similarly to the previous embodiment the LED's are defined by a dissimilar luminous intensity distribution angle. However, in contrast to the previous embodiment, the luminous intensity distribution angle of middle LED's 803, 804 is narrower than the luminous intensity distribution angle of the outside LED's 801, 802, 805, 806. Furthermore, and in even more contrast to the previous embodiment the LED's are defined by a dissimilar luminous intensity, which is higher for the middle LED's and lower for the outside LED's. Still in contrast to the previous embodiment the LED's are oriented on the mounting plate in such a manner, that only the middle LED's are directed parallel to the longitudinal axis of the head, while the outside LED's are slanted with respect thereto at an angle. In practice the outside LED's are directed in such a manner that their longitudinal axes define four edges of a pyramid having its imaged apex behind the mounting plate. In practice the slanting angle of the outside LED's is about 0.2-0.5 of their luminous intensity distribution angle. In addition to the above, the illumination module of the invention is provided with a dedicated electrical means for controlling current flowing through each LED and accordingly varying its luminous intensity. This means is shown in FIG. 7 as a block diagram, which will be discussed further in connection with the embodiment of the module shown in FIG. 8.

In this embodiment the slanted LED's 801, 802, 805, 806 are set to have relatively low luminous intensity since they are intended for illuminating of those regions of the body lumen, which are near to the optical head and therefore don't require excessive illumination. These LED's have a diameter of 1.5-2 mm.

The middle LED's are intended for illuminating distant regions of the body lumen and accordingly they should have a luminous intensity of at least one order of magnitude higher than the slanted LED's. In practice these LED's have a diameter of 3-5 mm.

In accordance with the invention the entire field of view, which is in front of the optical head, is divided into five separate virtual regions or windows, which refer to each LED and which illumination can be selectively controlled. The total field of view and the virtual regions are depicted in FIG. 6 by solid and dotted lines respectively. It is seen a square field of view 600 of the CCD sensor and four corner regions 601, 602, 605, 606 corresponding to four outside LED's 801, 802, 805, 806. Partially overlapping with the corner regions a coinciding middle regions 603, 604 corresponding to the middle LED's 803, 804 are also seen.

With the illumination module according to the embodiment shown in FIG. 8, it is possible to vary the luminous intensity of each LED and thus to control the level of illumination to which each virtual region is exposed. This is carried out by controlling the current flowing through respective LED in order to bring the illumination level associated with a respective virtual region to a coefficient expressing preset average value allocated to each virtual region. By virtue of this provision it is possibly to very significantly improve the illumination nonuniformity perceived by the optical sensor.

Now with reference to FIG. 7 the block diagram for controlling current supplied to each LED will be explained.

By virtue of the diagram the current supplied to each LED is individually controlled according to the amount of light reflected by those locations of the body lumen, which are observed by the optical head. This reflected light, which is schematically shown in FIG. 7 by parallel arrows passes the objective lens 34 and is sensed by a suitable sensor, e.g. the CCD sensor 28 or any other suitable sensor, which upon exposing it to light generates an analogous signal proportional to the amount of light. A video camera control board 710 is provided, which is electrically connected to a video splitter 700. The signal generated by the sensor is amplified and is split by the splitter into two signals. One of them proceeds to the video camera control board in which it is processed so as to be outputted as a standard PAL, NTSC, RGB, etc. video signal. The other signal proceeds to an image processing block 720, in which it is processed according to an algorithm, which ensures uniform illumination provided by each LED and thus ensures that each virtual region of the CCD sensor percieves the observed location of the body lumen without loosing information.

A synchro-splitter 730 is provided, which is controlled by the same signals and ensures that the signals received from the video splitter is processed in the image processing block 720 simultaneously and synchronously with scanning of the CCD sensor and that the signal processing is carried out synchronously with the scanning. By virtue of this provision it is possible to link between the signal produced by the sensor and the corresponding virtual region of the CCD sensor. In other words the algorithm divides the CCD sensor on the virtual regions and determines which virtual region should be taken care of in terms of its illumination level. As a result of the processing there are generated individual control signals, which are outputted by the image processing block to a plurality of controlled current source blocks (CCS blocks) supplying current required for the energizing of the LED's. Each CCS block produces current, which value is proportional to the corresponding control signal and to a difference between an instant signal produced by the respective CCD sensor and a coefficient, which refers to the preset value of the average illumination level of the virtual region.

It is seen in FIG. 7 that the connected in parallel LED's 801, 802, 805 and 806 are energized individually by respective CCS blocks 721, 722, 725, 726, while connected in series LED's 803, 804 are energized by a common CCS block 723. This arrangement might be advantageous for the illumination module in which two similar, centrally located LED's 803, 804 would illuminate distant locations of the body lumen.

Figure 9:
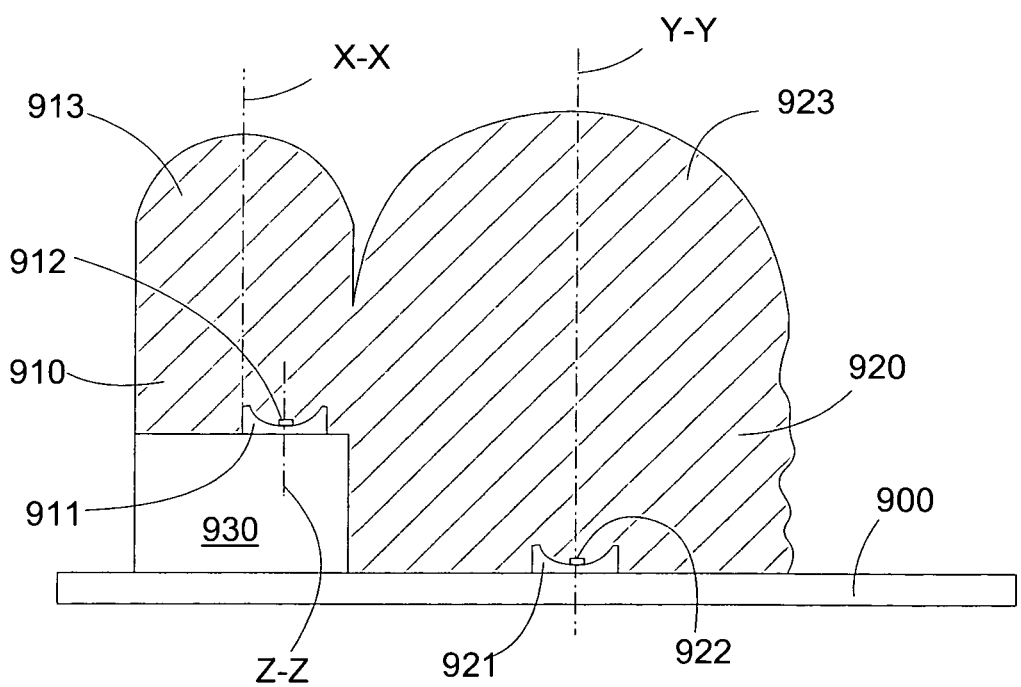
FIG. 9 schematically shows how illumination uniformity can be improved in accordance with still a further embodiment of the invention.

Now, with reference to FIG. 9 we will discuss another embodiment of the illuminating module fitted with LED's defined by dissimilar luminous intensity distribution angle. In FIG. 9 is depicted a portion of this module having at least two LED's 910, 920 of smaller and larger diameter. The LED's are mounted on a common mounting plate 900, which as in the previous embodiments is either a PCB or a hybrid ceramic plate. Each LED consists of a respective concave reflector 911, 921 with a semi conducting crystal 912, 922 deployed in the center of the reflector. It is seen also that reflector 911 of the small LED 901 resides on a pedestal 930. The reflector and the die of each LED is covered by a corresponding lens 913, 923. Each lens has respective longitudinal axis X-X and Y-Y. The lenses are made of a polymeric material, which is moldable and transparent or at least translucent. This material could be molded above the reflectors so as to encapsulate them inside and at the same time to integrate the encapsulated LED's with the mounting plate. To ensure that the LED's would have dissimilar luminous intensity distribution angle the reflector 911 of the LED 910 is situated on the pedestal eccentrically, i.e. the longitudinal axis X-X of the lens 913 is not co-axial with a longitudinal axis Z-Z of the LED 901. It should be kept in mind that a similar result could be achieved by shifting the longitudinal axis of the LED 921. Still further possibility for varying the luminous intensity distribution angle would be slanting of at least one of the LED's such that their longitudinal axes would be not parallel. This measure can be taken instead or in addition to the non coaxial disposition of the longitudinal axis of the lens with respect to the longitudinal axis of the LED.

From the above disclosure follows that the illumination nonuniformity of an illuminating module employing several LED's can be controlled by varying of at least one of the following parameters: luminous intensity of the LED's, luminous intensity distribution angle of the LED's, diameter of the LED's, direction of the LED's longitudinal axis. In accordance with the invention the illumination nonuniformity produced by such a module can be significantly improved if it has at least one LED having at least one parameter, which differs from the same parameter of the remaining LED's.

Figure 10:
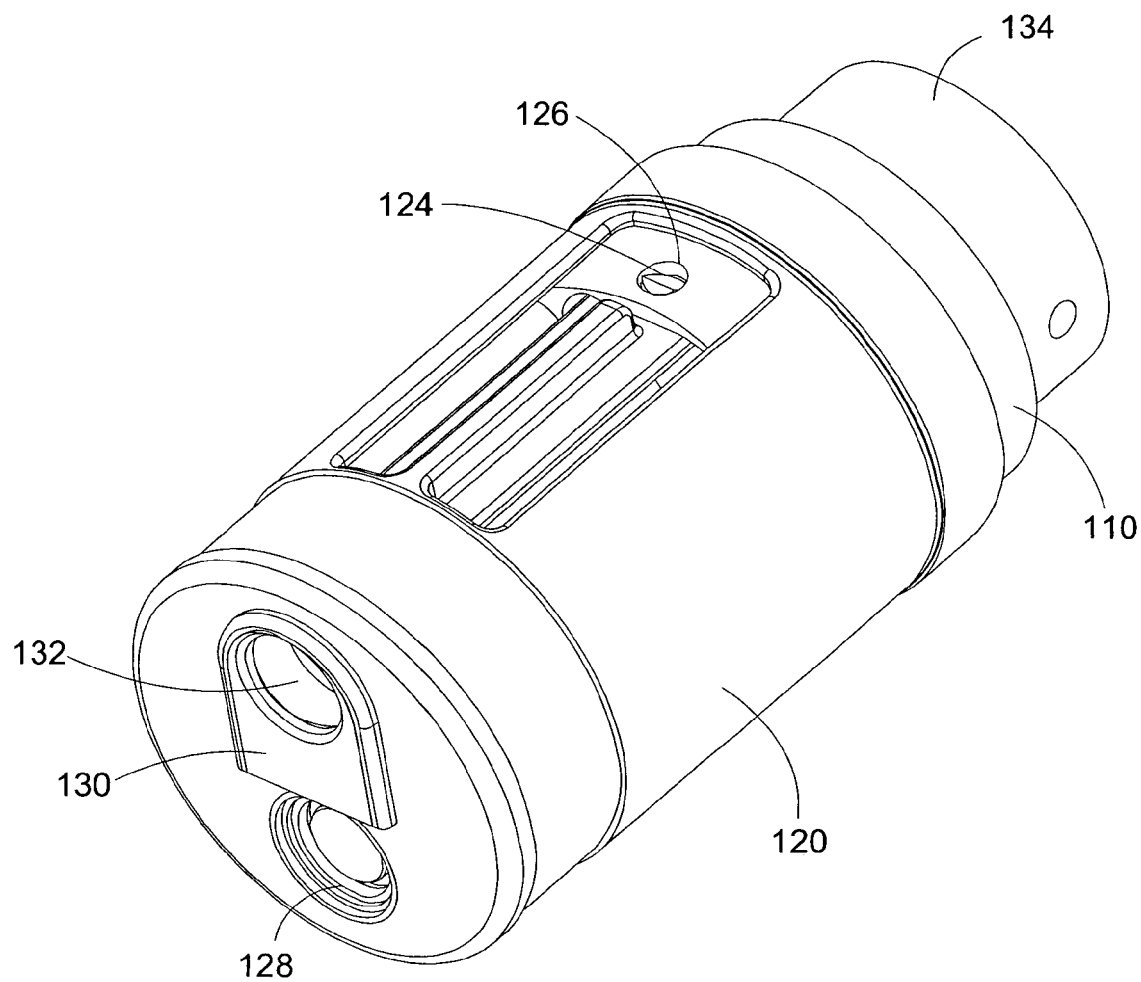
FIG. 10 is an isometric view of an optical head provided with a disposable cap.
Figure 11:
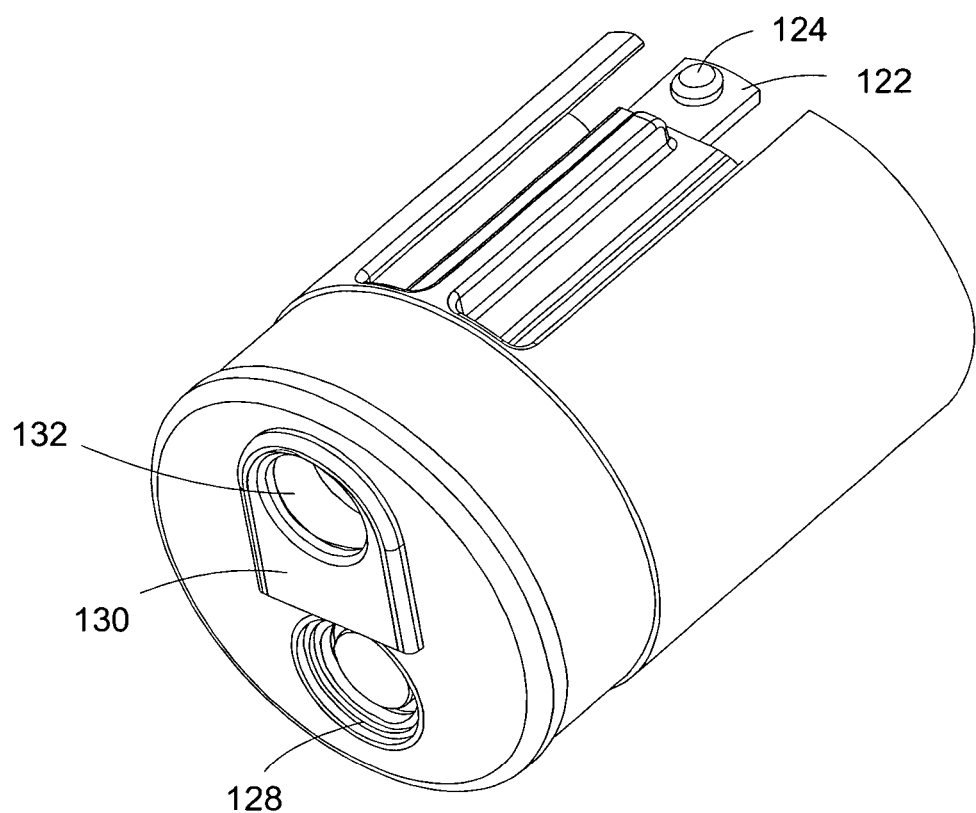
FIG. 11 is an isometric view of the disposable cap for the optical head shown in FIG. 10.
Figure 12A:
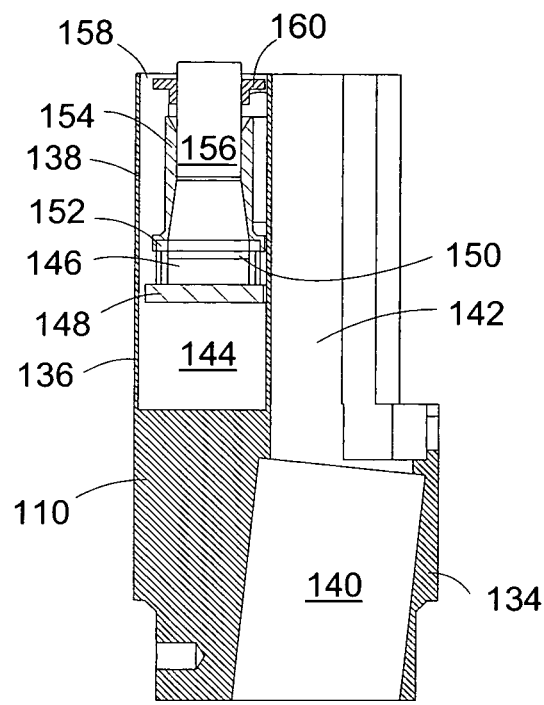
FIG. 12a is a longitudinal cross-sectional view of the optical head shown in FIG. 10 without the disposable cap.

Now referring to FIGS. 10,12a,b and 13 still further embodiments of the optical head of the invention will be disclosed. As seen in FIG. 10 the optical head comprises a main body portion 110 with a disposable cap 120 detachably attached thereto by a snap connection. The cap is seen in separate in FIG. 11. Such a cap would be advantageous for use with optical heads employed in the endoscopic apparatus provided with disposable inflatable propelling sleeve, e.g. as disclosed in our previous patent applications PCT/IL03/00661 or U.S. Ser. No. 60/570,607. Construction of the cap is not described in details here and it will be only mentioned that it is manufactured by injection molding from a suitable plastic material and is designed in such a manner that it can be conveniently attached to or detached from the head by virtue of a snap connection. This connection comprises a springy tongue 122 having protrusion 124 for entering into snapping engagement with a hole 126 made on the main body portion of the optical head. Situated on the distal end of the cap an aperture 128 for the objective lens is provided. Situated on the distal end of the cap and above the aperture a sprinkler shield 130 is provided. The sprinkler shield has an opening 132 for passing therethrough of a surgical tool when it is advanced through the multilumen tubing to the place of interest (not seen). It is not shown in details but should be appreciated that the sprinkler shield directs the water jet emerging from the irrigation channel of the multilumen tubing immediate on a window, which closes aperture 128.

Figure 12B:
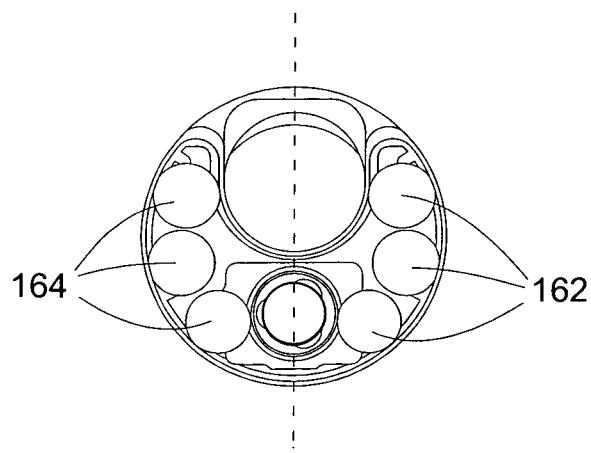
FIG. 12b is a left side view of the optical view shown in FIG. 10 without the disposable cap; and, FIG. 13 is an isometric view of the optical head without disposable cap.
Figure 13:
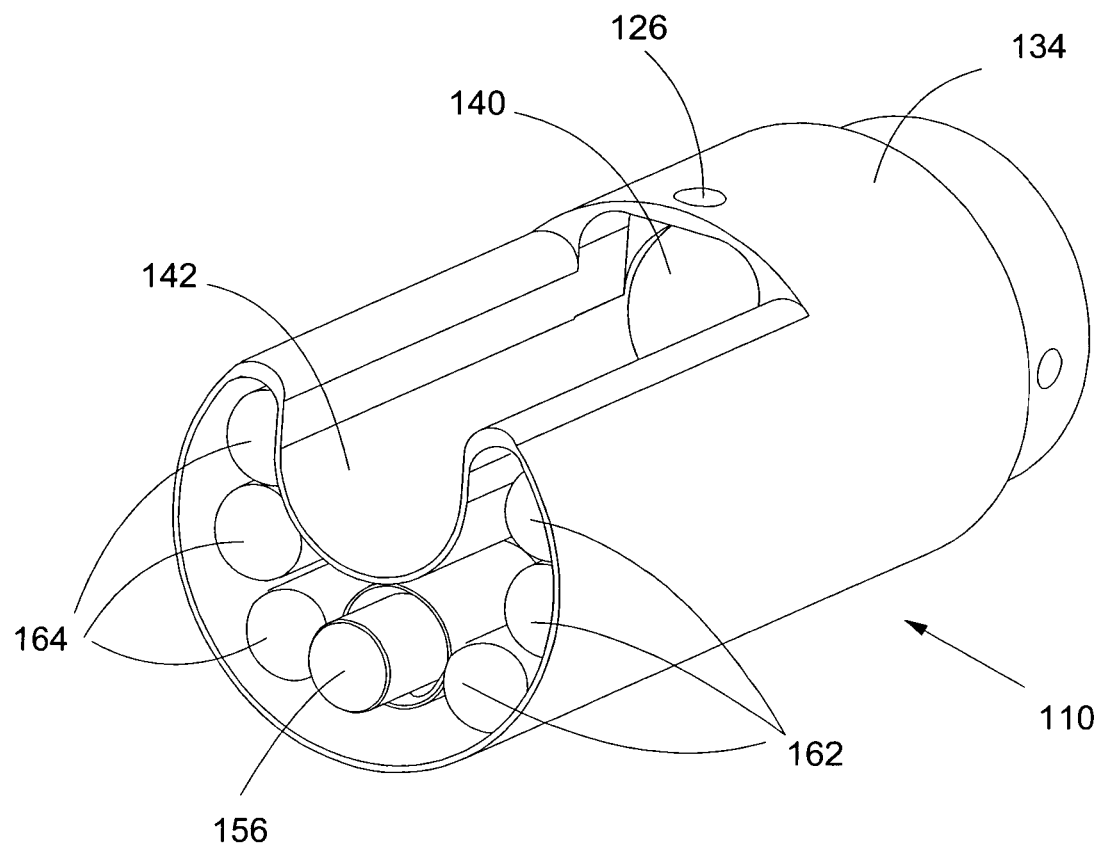

With reference to FIG. 12a it is seen that main body portion 110 is made as a single cylindrical part, which is provided with a rear end 134, a middle section 136 and a frontal end 138. Within the rear end a space 140 is provided for the guide channel. This space communicated with an U-like elongate depression 142, extending through the middle section and the frontal end of the main body portion. The purpose of the space 140 and of the elongate depression is similar to that of the passage 36 and the U-like depression 38 mentioned in connection with the embodiment depicted in FIG. 2. Within the middle section and within the frontal end a space 144 is provided, which accommodates therein a CCD sensor 146 attached to a PCB 148. In front of the CCD sensor a filter 150 is provided, which is covered by a translucent cover 152. The CCD sensor as well as the filter and the cover are retained in place by a rear end of a retaining bushing 154, while the frontal end of the bushing retains an objective lens 156, which slightly protrudes outside the frontal end 138 through an opening 158. The arrangement being such that when the cap is attached to the optical head the window 158 is in alignment with the window 128 of the cap. Situated on the forward most end of the objective lens a parasitic light protector is provided comprising an antiglare ring 160. Referring now to FIGS. 12b and 13 it is seen that within the main body portion are deployed six LED's, which are divided in two groups arranged symmetrically with respect to an imaginary middle plane of the main body portion (shown by dashed line). The groups of LED's are collectively designed by respective reference numerals 162 and 164. It is not shown in details, but should be appreciated that the LED's are mounted on a common mounting plate having saddle-like shape so as to conveniently reside within the head as an illuminating module, similar to those already described. The illuminating nonuniformity of such a module could be controlled by the same four parameters, which were mentioned before. Among these parameters are: luminous intensity, luminous intensity distribution angle, size, and direction of longitudinal axis.

It should be appreciated that the present invention is not limited to the above-described embodiments and that changes and one ordinarily skilled in the art can make modifications without deviation from the scope of the invention, as will be defined in the appended claims. Below are some examples of alternative implementation of some aspects of the invention.

It is not compulsory that the LED's are arranged symmetrically with respect to the middle plane of the optical head (as seen in FIGS. 4, 5, 8, 12b). In a situation when there is only limited space available the distal end of the working channel can be twisted at some degrees to allow arranging three LED's at one side of the middle plane and two LED's at the opposite side. Still further possibility for deployment the LED's within the head would be locating them at a different distance from the forward most end of the head. For example two LED's of each group could be situated closer to the forward most end than the third LED. By virtue of this provision it is possible to retain symmetrical disposition of the LED's with respect to the middle plane.

Instead of the snap connection described above one can contemplate snap connection, in which the optical head is provided with the tongue and the hole is made in the cap.

Instead of protrusion the tongue can be provided with a hole or depression and the mating protrusion can be arranged on the optical head.

Furthermore, instead of using the snap connection one could use any other suitable meachnical connection as known in the art.

It should be kept in mind also, that the present invention is not limited strictly to optical heads employed in colonoscopes. The present invention covers any other endoscopic apparatuses used for the purpose of examination, operation, diagnostic, therapy etc. Among such endoscopic apparatuses one can mention endoscopes for examination of esophagus, stomach and duodenum, cystoscopes for examinating the bladder, angioscopes, bronchoscopes, laparoscopes, arthroscopes, sigmoidoscopes etc. Furthermore the present invention covers not only medical, but also industrial applications and is applicable in industrial endoscopes, or so-called boroscopes.

It should also be appreciated that the features disclosed in the foregoing description, and/or in the following claims, and/or in the accompanying drawings may, both separately and in any combination thereof, be material for realizing the present invention in diverse forms thereof.

We claim:

1. An optical head for an endoscope, the optical head comprising:
    an imaging system comprising
        a CCD-chip or CMOS; and
    an illuminating system comprising
        an illuminating module fitted with a first illumination means and a second illumination means substantially simultaneously illuminating, wherein the first illumination means and the second illumination means have different luminous intensity distribution angles thereby exhibiting a uniform illumination,
        wherein the first and second illuminating means are LEDs and the illuminating module comprises a mounting plate on which the LEDs are deployed, wherein the LEDs are divided into two groups located respectively at a left side and a right side of an imaginary longitudinal middle plane of the optical head, and
    wherein the mounting plate has a saddle-like configuration and each of the groups of LEDs is located within a respective arched region provided at the left and the right side of the imaginary longitudinal middle plane.

2. The optical head according to claim 1, wherein the mounting plate comprises a ceramic hybrid module.

3. The optical head according to claim 1, wherein the LEDs are situated symmetrically with respect to the imaginary longitudinal middle plane.

4. The optical head according to claim 3, wherein the LEDs are secured on the mounting plate such that their longitudinal axes are directed parallel to the longitudinal axis of the optical head.

5. The optical head according to claim 1, wherein the first illumination means comprises a middle LED and the second illumination means comprises outside LEDs, and wherein the luminous intensity distribution angle of the middle LED is wider than the luminous intensity distribution angle of the outside LEDs.

6. The optical head according to claim 1, wherein the first illumination means comprises a middle LED and the second illumination means comprises outside LEDs, and wherein the LEDs are secured on the mounting plate in such a manner that longitudinal axes of the outside LEDs are directed not parallel to the longitudinal axis of the optical head.

7. The optical head according to claim 6, wherein the diameter of the middle LED is larger than the diameter of the outside LEDs.

8. The optical head according to claim 6, wherein the luminous intensity distribution angle of the middle LED is narrower than the luminous intensity distribution angle of the outside LEDs.

9. The optical head according to claim 6, wherein the luminous intensity of the middle LED is not equal to the luminous intensity of the outside LEDs.

10. The optical head according to claim 1, further comprising a means for controlling the luminous intensity of the LEDs.

11. The optical head according to claim 10, wherein the CCD-chip has a field of view, which is divided into virtual regions that are associated with respective LEDs and the means for controlling the luminous intensity comprises at least one current source supplying a current to a respective LED, the current depends on a preset value of the average illumination level of the virtual region associated with this LED.

12. The optical head according to claim 1, further comprising a disposable cap detachably connectable to the optical head.

13. The optical head according to claim 12, in which the optical head is detachably connectable to the cap by a snap connection.

14. The optical head according to claim 13, wherein the snap connection comprises an elastically deflectable tongue for engagement with a hole.

15. A method for controlling an optical head of an endoscope, the optical head comprising an imaging system comprising a solid state imaging sensor, and an illuminating system comprising an illuminating module fitted with several illuminating means, including a first illumination means and a second illumination means substantially simultaneously illuminating, wherein the first illumination means and the second illumination means have different luminous intensity distribution angles, wherein the first and second illuminating means are LEDs and the illuminating module comprises a mounting plate on which the LEDs are deployed, wherein the LEDs are divided into two groups located respectively at a left side and a right side of an imaginary longitudinal middle plane of the optical head, and wherein the mounting plate has a saddle-like configuration and each of the groups of LEDs is located within a respective arched region provided at the left and the right side of the imaginary longitudinal middle plane, the method comprising:

dividing the field of view of the imaging sensor into virtual regions that are associated with respective illuminating means; and supplying electrical current to a respective illuminating means depending on the average illumination level of the virtual region associated with the respective illuminating means.

16. An optical head for an endoscope, the optical head comprising:

an imaging system comprising
        a CCD-chip or CMOS; and
    an illuminating system comprising
        an illuminating module fitted with a plurality of LEDs divided into two groups, each of the groups of LEDs consisting of two outside LEDs and a middle LED, at least one of the LEDs defined by a parameter value different from a value of the same parameter for remaining LEDs, the illuminating module comprising a mounting plate on which the LEDs are secured such that their longitudinal axes are directed parallel to the longitudinal axis of the optical head, wherein the two groups of LEDs are located respectively at a left side and a right side of an imaginary longitudinal middle plane of the optical head, wherein the mounting plate has a saddle-like configuration and each of the two groups of LEDs is located within a respective arched region provided at the left and the right side of the imaginary longitudinal middle plane, wherein the LEDs are situated symmetrically with respect to the imaginary longitudinal middle plane, and wherein the luminous intensity distribution angle of the middle LED is different from the luminous intensity distribution angle of the outside LEDs.

17. The optical head according to claim 16, wherein the luminous intensity distribution angle of the middle LED is wider than the luminous intensity distribution angle of the outside LEDs.

18. An optical head for an endoscope, the optical head comprising:

an imaging system comprising
        a CCD-chip or CMOS; and
    an illuminating system comprising
        an illuminating module fitted with a plurality of LEDs divided into two groups, each of the groups of LEDs consisting of two outside LEDs and a middle LED, at least one of the LEDs defined by a parameter value different from a value of the same parameter for remaining LEDs, the illuminating module comprising a mounting plate on which the two groups of LEDs are secured in such a manner that longitudinal axes of the outside LEDs are directed not parallel to the longitudinal axis of the optical head, wherein the two groups of LEDs are located respectively at a left side and a right side of an imaginary longitudinal middle plane of the optical head, wherein the mounting plate has a saddle-like configuration and each of the two groups of LEDs is located within a respective arched region provided at the left and the right side of the imaginary longitudinal middle plane, wherein the LEDs are situated symmetrically with respect to the imaginary longitudinal middle plane, and wherein the diameter of the middle LEDs is larger than the diameter of the outside LEDs.

19. An optical head for an endoscope, the optical head comprising:

an imaging system comprising
        a CCD-chip or CMOS; and
    an illuminating system comprising
        an illuminating module fitted with a plurality of LEDs divided into two groups, each of the groups of LEDs consisting of two outside LEDs and a middle LED, at least one of the LEDs defined by a parameter value different from a value of the same parameter for remaining LEDs, the illuminating module comprising a mounting plate on which the LEDs are secured in such a manner that longitudinal axes of the outside LEDs are directed not parallel to the longitudinal axis of the optical head, wherein the two groups of LEDs are divided located respectively at a left side and a right side of an imaginary longitudinal middle plane of the optical head, wherein the mounting plate has a saddle-like configuration and each of the two groups of LEDs is located within a respective arched region provided at the left and the right side of the imaginary longitudinal middle plane, wherein the LEDs are situated symmetrically with respect to the imaginary longitudinal middle plane, and wherein the luminous intensity distribution angle of the middle LED is narrower than the luminous intensity distribution angle of the outside LEDs.

* * * * *